(12) United States Patent
Liao

(10) Patent No.: US 10,082,281 B1
(45) Date of Patent: Sep. 25, 2018

(54) OMNIDIRECTIONAL LIGHTING STAND

(71) Applicant: LIH YANN INDUSTRIAL CO., LTD., Taichung (TW)

(72) Inventor: Po Lin Liao, Taichung (TW)

(73) Assignee: LIH YANN INDUSTRIAL CO., LTD., Taichung (TW)

( * ) Notice: Subject to any disclaimer, the term of this patent is extended or adjusted under 35 U.S.C. 154(b) by 71 days.

(21) Appl. No.: 15/459,006

(22) Filed: Mar. 15, 2017

(51) Int. Cl.
| F21V 21/28 | (2006.01) |
| F21V 21/22 | (2006.01) |
| F21V 21/108 | (2006.01) |
| F21S 6/00 | (2006.01) |
| F21L 4/00 | (2006.01) |
| F21V 21/14 | (2006.01) |
| F21Y 115/10 | (2016.01) |
| G01N 21/88 | (2006.01) |

(52) U.S. Cl.
CPC ............... F21V 21/28 (2013.01); F21L 4/00 (2013.01); F21S 6/005 (2013.01); F21V 21/108 (2013.01); F21V 21/145 (2013.01); F21V 21/22 (2013.01); F21Y 2115/10 (2016.08); G01N 21/8806 (2013.01)

(58) Field of Classification Search
CPC .......... F21V 21/22; F21V 21/26; F21V 21/28; F21V 21/29; F21V 21/30; F21V 21/108; F21V 21/145; F21L 4/00; F21S 6/004; F21S 6/005; F21S 6/006
See application file for complete search history.

(56) References Cited

U.S. PATENT DOCUMENTS

| 4,232,357 A | * | 11/1980 | Dietz | ...................... F21L 14/04 362/191 |
| 5,424,931 A | * | 6/1995 | Wheeler | ................. F21S 6/006 362/249.1 |
| 6,019,484 A | * | 2/2000 | Seyler | ..................... F21L 14/04 362/287 |
| 6,854,862 B1 | * | 2/2005 | Hopf | ....................... F21L 14/04 362/220 |
| 7,073,926 B1 | * | 7/2006 | Kremers | ................ F16M 11/10 248/123.2 |
| 8,322,877 B1 | * | 12/2012 | Merritt | .................... F21L 14/04 362/220 |
| 2009/0225536 A1 | * | 9/2009 | Emmert | .................. F21L 14/04 362/220 |
| 2009/0284963 A1 | * | 11/2009 | Intravatola | ............. F16M 11/28 362/190 |
| 2015/0192243 A1 | * | 7/2015 | Sharrah | .................. F16M 11/28 362/190 |

* cited by examiner

*Primary Examiner* — Alan Cariaso
(74) *Attorney, Agent, or Firm* — Andrew C. Cheng

(57) ABSTRACT

An omnidirectional lighting stand includes a base structure, an extendible post structure, a pitch-rotation structure, and a light arm structure. The light arm structure is rotatably mounted to the pitch-rotation structure. The pitch-rotation structure is mounted to a top end of the extendible post structure. The extendible post structure has a lower end mounted to the base structure. The pitch-rotation structure is rotatably mounted to a rotation seat for adjustment of a pitch angle thereof in a range of 180 degrees and is selectively fixe din position by a handle bolt. The pitch-rotation structure has a front-rear through hole provided for adjustment of a lighting direction of the lighting device in an angular range of 360 degrees.

4 Claims, 8 Drawing Sheets

OMNIDIRECTIONAL LIGHTING STAND

BACKGROUND OF THE INVENTION

1. Field of the Invention

The present invention relates to the field of lighting and illumination, and more particularly to an omnidirectional lighting stand.

2. The Related Arts

A known lighting stand is shown in FIG. 1, generally designated at 50. The known lighting stand 50 comprises a support 15 in the form of a tripod. Mounted on the support 50 is an extendible light post 52 on which a lighting device 53 is mounted to provide lighting for visual inspection and performance various operations on an automobile.

However, the known lighting stand 50 often cause inconvenience in use for the support 51 may prevent the lighting stand from being positioned very close to an automobile. In addition, no casters are provided so that moving the lighting stand is inconvenient. In addition, no angle adjusting means is provided so that it is not possible to make adjustment of the lighting direction of the lighting stand to project light in for example a top-down direction or a bottom-up direction, nor is the lighting directed to irradiate the automobile roof at a short distance. Further, no space is provided in the lighting stand to accommodate a battery so that power supply, such as an external battery, must be located externally and made through a cable to the lighting device with an extended length of the cable generally required. Apparently, such a known lighting stand 50 must be further improved to suit the needs of general users.

In consideration of the drawbacks of the prior art discussed above, it is a challenge of those involved in this field to provide a novel structure that helps overcome or alleviates the above problems.

In view of this, the present invention aims to provide a technical solution that overcomes the drawbacks of the prior art.

SUMMARY OF THE INVENTION

The primary objective of the present invention is to provide an omnidirectional lighting stand, which comprises a base structure made with a low-profile configuration and an extendible post structure in an eccentric arrangement so as to allow the extendible post structure to be positioned close to an automobile, wherein a light arm structure is rotatable for adjustment of a pitch angle a range of 180 degrees and a lighting device is adjustable for angular range of lighting direction in a range of 360 degrees so that omnidirectional lighting can be achieved and the lighting stand can be broken down for easy DIY assembly, making packaging and shipping easy and convenient.

To achieve the above objective, the present invention provides an omnidirectional lighting stand, which comprises: a base structure, an extendible post structure, a pitch-rotation structure, and a light arm structure, wherein the light arm structure is rotatably mounted to the pitch-rotation structure; the pitch-rotation structure is mounted to a top end of the extendible post structure; a lower end of the extendible post structure is mounted to the base structure; the base structure comprises two elongate rods extending outward to form a V-shape, upper and lower boards, which are generally triangular in shape and fix a divergent end of the two elongate rods, and a T-shaped member comprising a bar that is fixed by the upper and lower boards and arranged in the divergent end of the two elongate rods, all being fastened together by bolts to form the base structure; casters are mounted to two ends of a cross rod of the T-shaped member and free ends of the two elongate rods; the T-shaped member has a top side on which a battery support tray is securely mounted and an upright columnar frame is fixedly mounted atop the upper board; the extendible post structure comprises a large-diameter non-circular rod in which a small-diameter non-circular rod is telescopically received, a sleeve fit to a top end of the large-diameter non-circular rod, a rear locking bolt fastening the sleeve and the large-diameter non-circular rod and abutting a protection plate that is positioned tightly against the small-diameter non-circular rod; the light arm structure comprises a lighting device attached to a front end of an arm rod and a circular rod having a grip and fit with a circular ring to allow the circular rod to be coupled to a rear end of the arm rod; the pitch-rotation structure comprises two retention plates mounted to a top end of the small-diameter non-circular rod, a nut attached to one of the retention plates, a rotation seat arranged between the two retention plates, and a handle bolt extending through holes formed in the two retention plates and leftward and rightward through holes of the rotation seat to engage with and be fastened to the nut, the rotation seat being provided with a front-rear through hole, and an open slot located above the front-rear through hole, wherein the open slot is provided for receiving extension of the circular rod of the light arm structure, an L-shaped bolt being fastened to the open slot to fix a lighting direction of the lighting device and allowing for adjustment of an angular range of the lighting direction of the lighting device in a range of 360 degrees. The base structure has a low-profile configuration and the extendible post structure is set up as an eccentric arrangement so that the omnidirectional lighting stand is allowed to move to a location where the extendible post structure is close to an automobile, allowing the lighting to be projected, in an optimum way, onto the automobile to provide illumination necessary for performance of for example an automobile beautification operation.

BRIEF DESCRIPTION OF THE DRAWINGS

The present invention can be fully understood from the following detailed description and preferred embodiments with reference to the accompanying drawings, in which.

DETAILED DESCRIPTION OF THE PREFERRED EMBODIMENTS

The present invention provides an omnidirectional lighting stand.

To better expound the purposes, features, and effectiveness of the present invention to help better understand and appreciate the present invention, description will be given below with reference to embodiments and drawings of the present invention.

Figure 1:
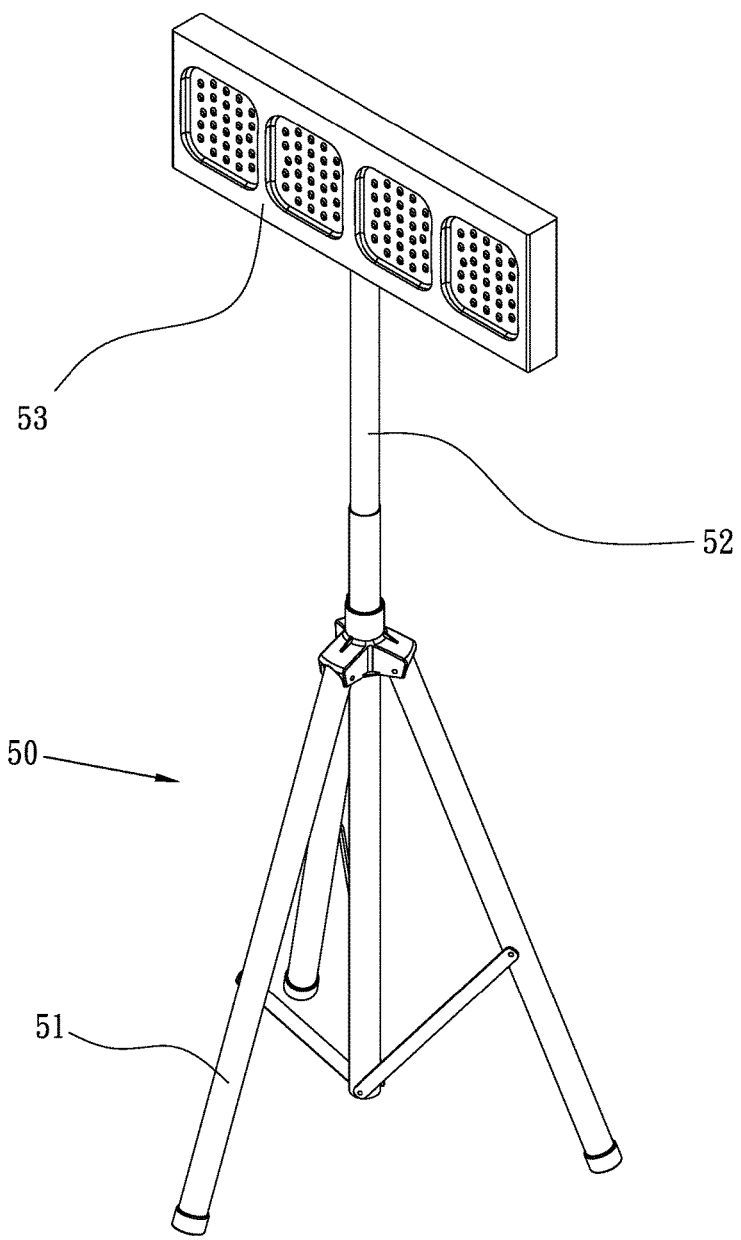
FIG. 1 is a perspective view showing a conventional lighting stand.
Figure 2:
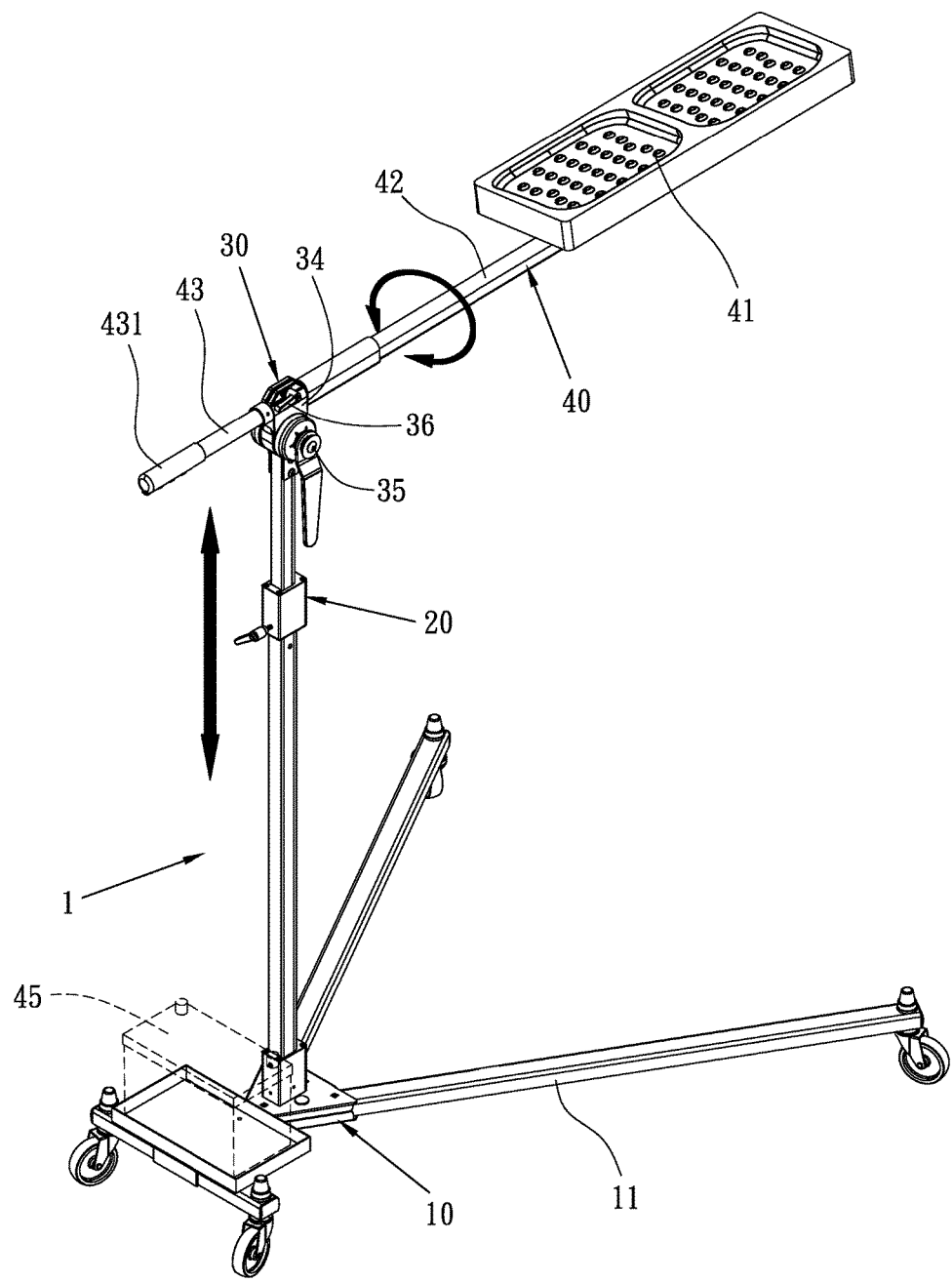
FIG. 2 is a schematic view showing an embodiment of the present invention in a condition of lighting upwards.

Referring to FIG. 2, the present invention provides an omnidirectional lighting stand, which comprises the following components/parts, details of which will be described as follows.

Figure 7:
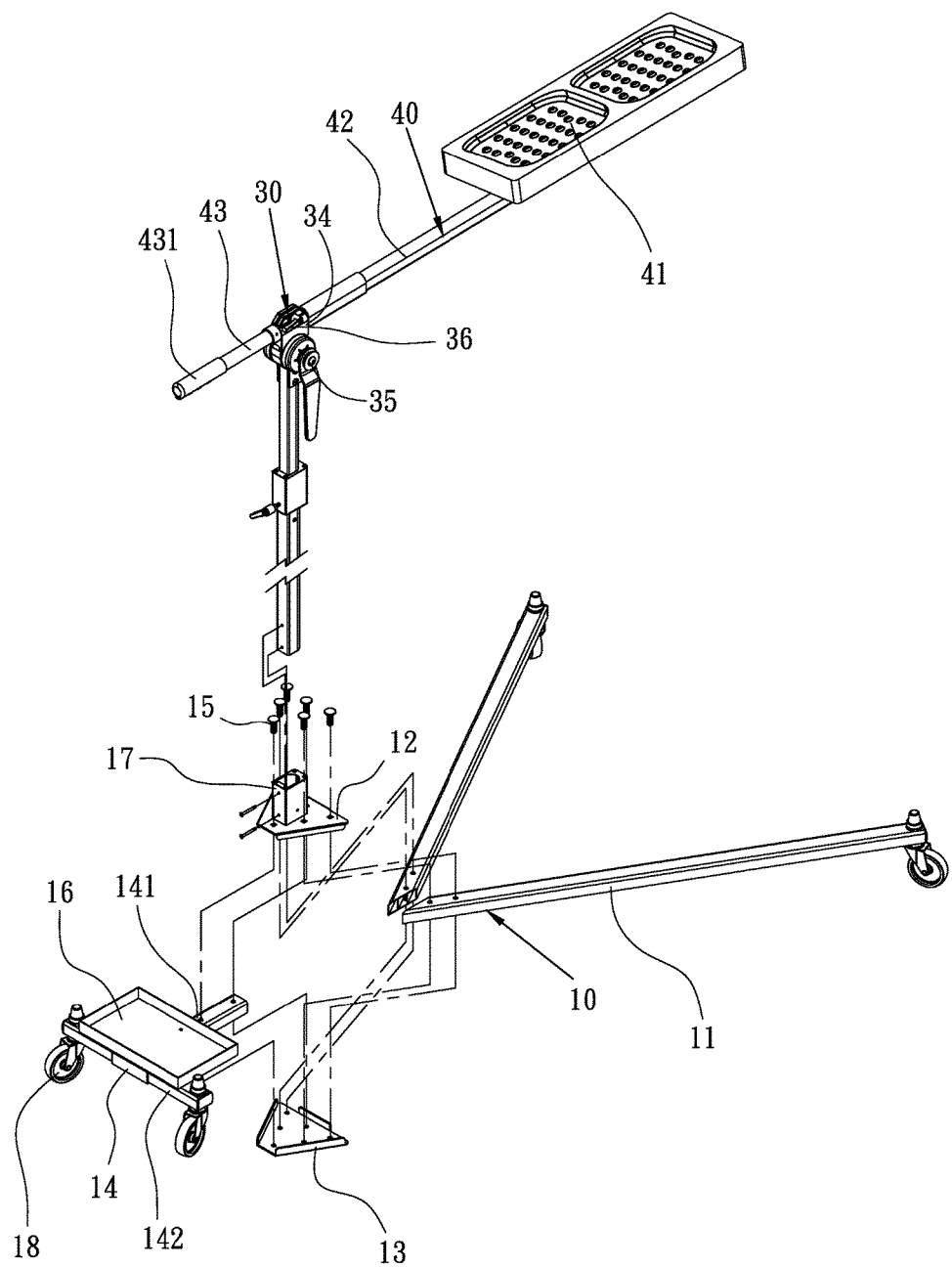
FIG. 7 is an exploded view illustrating a base of the embodiment of the present invention.

Referring to FIG. 7, a base structure 10 comprises two elongate rods 11, which are arranged to extend outward to form a V-shape, upper and lower boards 12, 13, which are generally triangular in shape and fix a divergent end of the two elongate rods 11, and a T-shaped member 14 comprising a bar 141 that is fixed by the upper and lower boards 12, 13 and arranged in the divergent end of the two elongate rods 11, all being fastened together by a plurality of bolts 15, wherein the T-shaped member 14 has a top side on which a battery support tray 16 is securely mounted and an upright columnar frame 17 is fixedly mounted atop the upper board 12.

Figure 6:
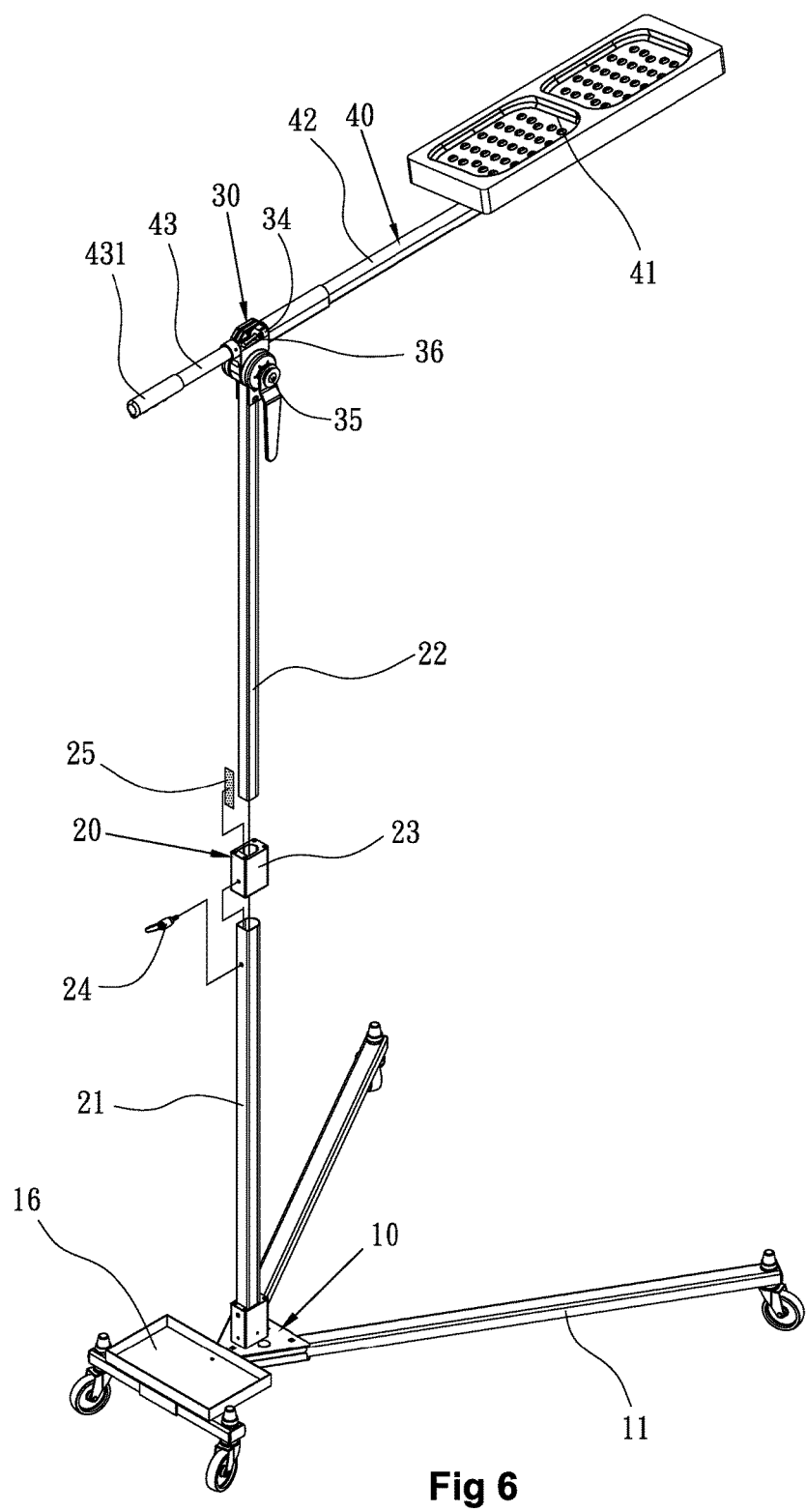
FIG. 6 is an exploded view illustrating an extendable post of the embodiment of the present invention.

Referring to FIG. 6, an extendible post structure 20 comprises a large-diameter non-circular rod 21, which is of a tubular form in which a small-diameter non-circular rod 22 is telescopically received, a sleeve 23, which is fit to a top end of the large-diameter non-circular rod 21, a rear locking bolt 24 fastening the sleeve 23 and the large-diameter non-circular rod 21 and abutting a protection plate 25, preferably made of steel, that is positioned tightly against the small-diameter non-circular rod 22 to protect a surface of the small-diameter non-circular rod 22, wherein the rear locking bolt 24 is selectively released to allow for extension and retraction of the small-diameter non-circular rod 22 for height adjustment.

Figure 5:
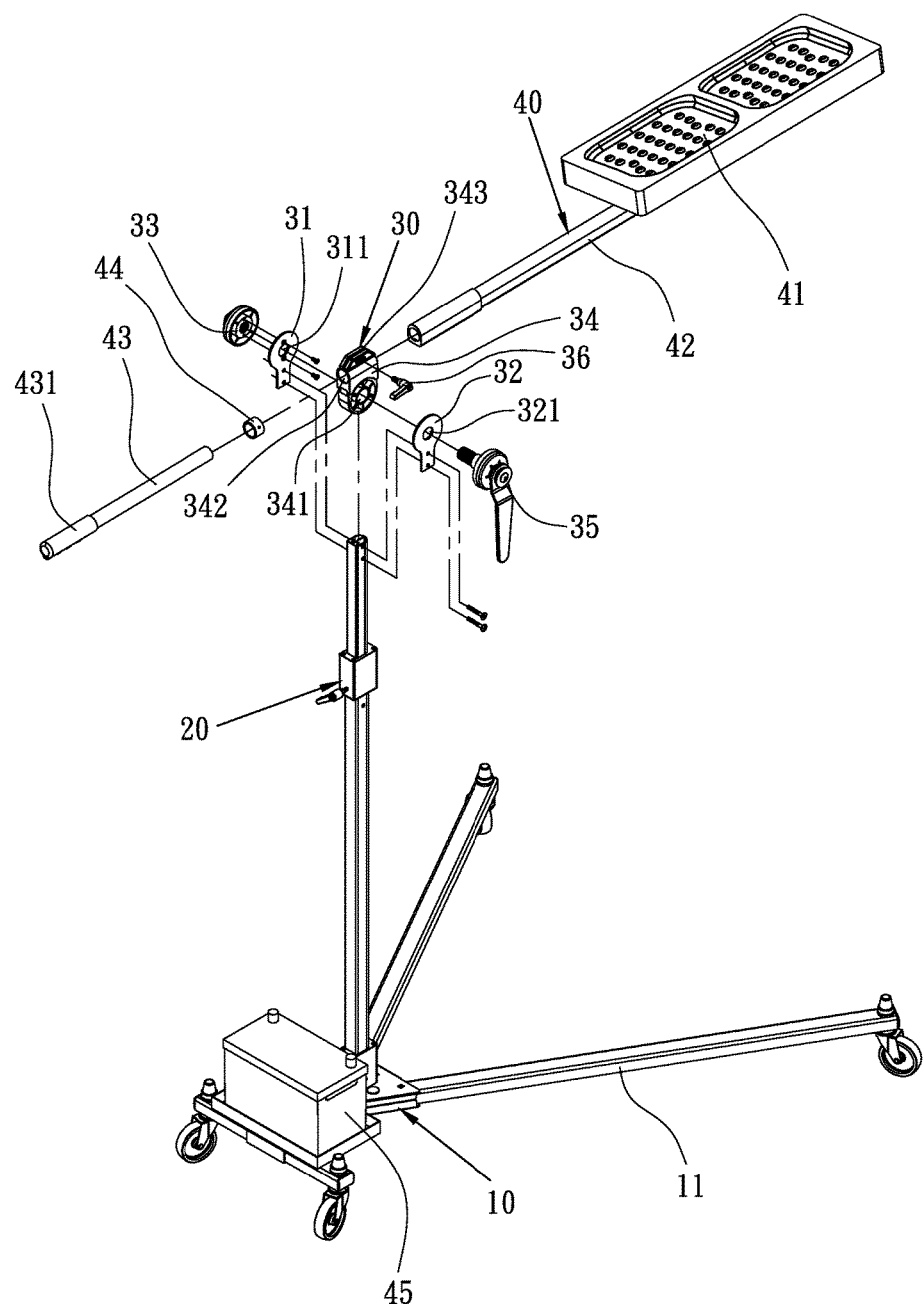
FIG. 5 is an exploded view illustrating a pitch-rotation structure of the embodiment of the present invention.

Referring to FIG. 5, a pitch-rotation structure 30 comprises two retention plates 31, 32 that are mounted to a top end of the small-diameter non-circular rod 22, a nut 33 attached to one of the retention plates 31, a rotation seat 34 arranged between the two retention plates 31, 32, and a handle bolt 35 extending, generally in a pitch axis, through holes 311, 321 defined in the two retention plates 31, 32 and leftward and rightward through holes 341 of the rotation seat 34 to engage with and be fastened to the nut 33.

Figure 4:
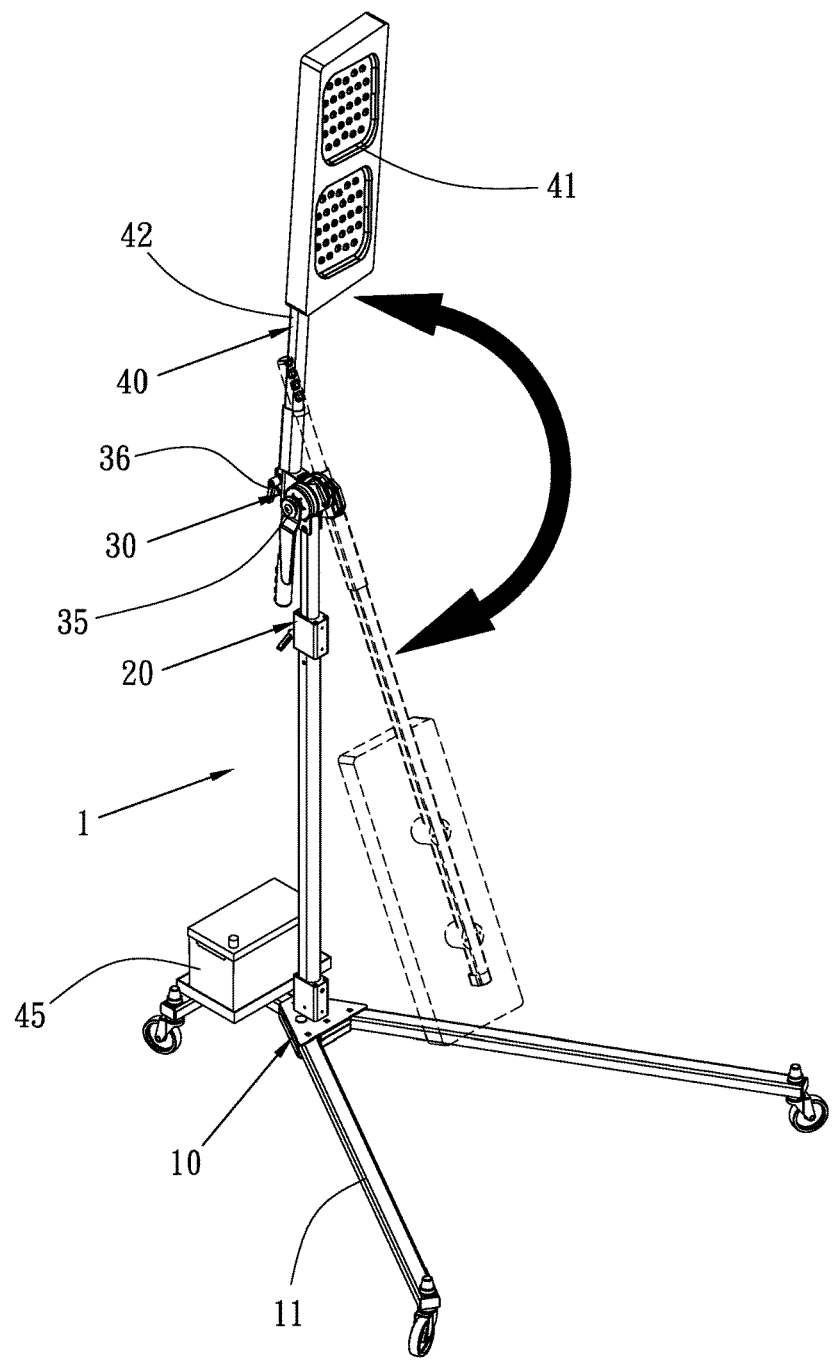
FIG. 4 is a schematic view illustrating pitch rotation of the embodiment of the present invention.

Referring to FIG. 4, releasing the handle bolt 35 allows the rotation seat 34 to pitch-rotate up and down in an angular range of preferably 180 degrees. The rotation seat 34 is provided with a front-rear through hole 342 generally extending in a roll axis and an open slot 343 located above the front-rear through hole 342.

Referring to FIG. 5, a light arm structure 40 comprises a lighting device 41 attached to a front, free end of an arm rod 42 and a circular rod 43 having a grip 431, wherein the circular rod 43 is first fit with a circular ring 44 and a free end of the circular rod 43 extends through the front-rear through hole 342 to allow the free end of the circular rod 43 to be coupled to rear end of the arm rod 42, so that the front-rear through hole 342 receives the circular rod 43 of the light arm structure 40 to extend therethrough.

Figure 3:
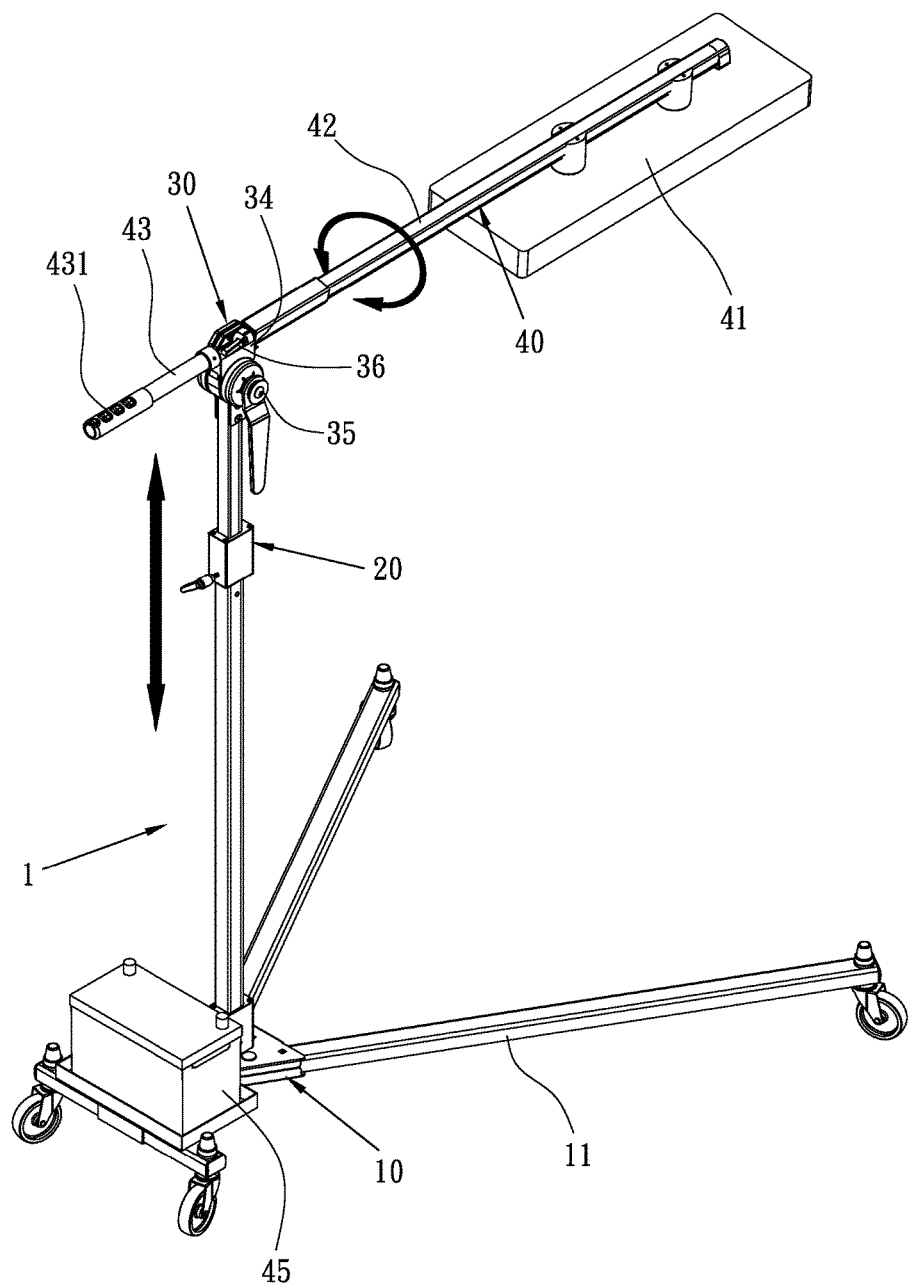
FIG. 3 is a schematic view showing an embodiment of the present invention in a condition of lighting downwards.

Referring to FIGS. 2 and 3, an L-shaped bolt 36 is fastened to the open slot 343 in order to selectively fix a lighting direction of the lighting device 41 so that releasing the bolt allows for adjustment of the lighting direction the lighting device 41 in an angular range of a full circle of 360 degrees. The light arm structure 40 is rotatably mounted to the pitch-rotation structure 30, and the pitch-rotation structure 30 is mounted to a top end of the extendible post structure 20, while a lower end of the extendible post structure 20 is mounted to the upright columnar frame 17 of the base structure 10 to make up the omnidirectional lighting stand 1.

Figure 8:
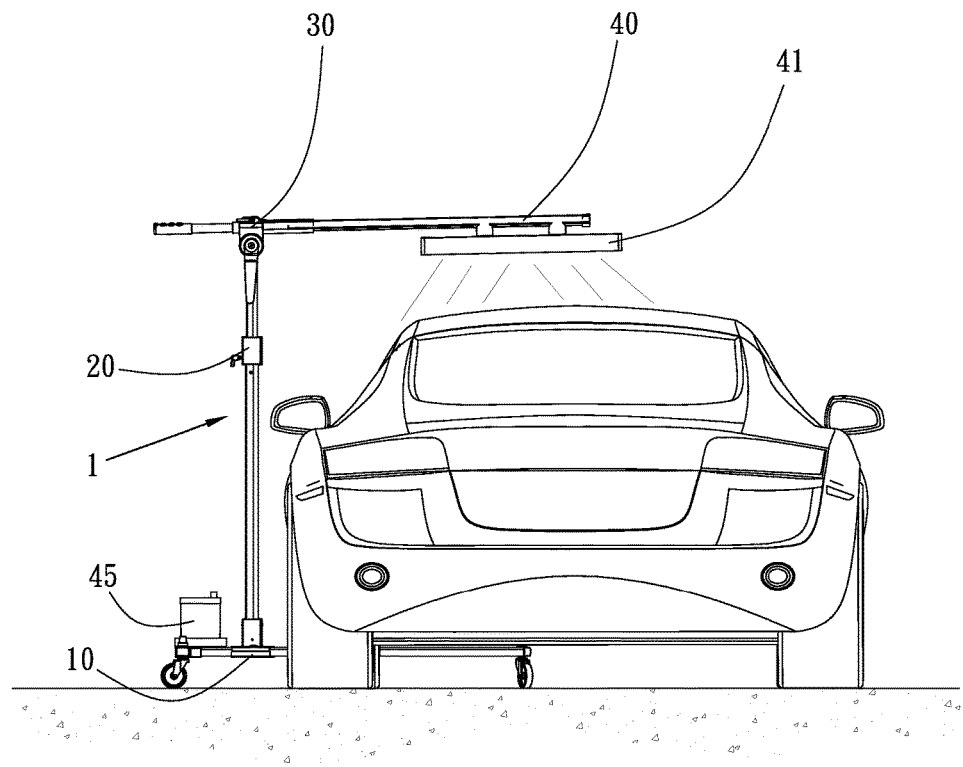
FIG. 8 is a schematic view showing an application of the embodiment of the present invention to an operation of lighting an automobile for visual inspection of beautification and painting of the automobile.

Referring to FIG. 8, the base structure 10 has a low-profile configuration and the extendible post structure 20 is set up as an eccentric arrangement so that the omnidirectional lighting stand 1 is allowed to move to a location where the extendible post structure 20 is close to an automobile, allowing the lighting to be projected, in an optimum way, onto the automobile to provide illumination necessary for performance of for example an automobile beautification operation.

Referring to FIG. 7, in the omnidirectional lighting stand, the T-shaped member 14 comprises a cross rod 142, wherein casters 18 are respectively mounted to two opposite ends of the cross rod and free ends of the two elongate rods 11.

Referring to FIG. 3, in the omnidirectional lighting stand, the battery support tray 16 is provided to receive a battery 45 positioned thereon such that the battery 45 is electrically connectable to the lighting device 41 for supply of electrical power thereto.

Referring to FIG. 2, in the omnidirectional lighting stand, the lighting device 41 may comprise a light-emitting diode (LED) based lighting device. The omnidirectional lighting stand 1 can be easily disassembled for easy packaging in a workshop and also allowing a user to easily do DIY assembly after purchasing the lighting stand. Grips or handles are involved in the lighting stand to allow for easy adjustment of the pitch angle of the lighting device and also for improving perception of quality thereof. Parts can be made of aluminum extruding to provide better tightness and better hand touch feeling so as to improve overall quality and to make packaging and shipping easy. The lighting device 41 can be placed extremely close to an automobile roof for close surface lighting, making it better suit the need for automobile beautification operation.

Illustrated above are the embodiments of the present disclosure, which should not be considered limitative to the scope of the invention. Therefore, any equivalent substitutions or variations to the structures or processes disclosed in the specification and the drawing of the present disclosure, or a direct or indirect application of the invention to the other technical fields should be considered as part of the present disclosure.

What is claimed is:

1. An omnidirectional lighting stand, comprising:
    a base structure, which comprises two elongate rods extending outward to form a V-shape, upper and lower boards, which are generally triangular in shape and fix a divergent end of the two elongate rods, and a T-shaped member comprising a bar that is fixed by the upper and lower boards and arranged in the divergent end of the two elongate rods, all being fastened together by bolts, wherein the T-shaped member has a top side on which a battery support tray is securely mounted and an upright columnar frame is fixedly mounted atop the upper board;
    an extendible post structure, which comprises a large-diameter non-circular rod in which a small-diameter non-circular rod is telescopically received, a sleeve fit to a top end of the large-diameter non-circular rod, a rear locking bolt fastening the sleeve and the large-diameter non-circular rod and abutting a protection plate that is positioned tightly against the small-diameter non-circular rod to protect a surface of the small-diameter non-circular rod, wherein the rear locking bolt is selectively released to allow for extension and retraction of the small-diameter non-circular rod for height adjustment;

a pitch-rotation structure, which comprises two retention plates mounted to a top end of the small-diameter non-circular rod, a nut attached to one of the retention plates, a rotation seat arranged between the two retention plates, and a handle bolt extending through holes formed in the two retention plates and leftward and rightward through holes of the rotation seat to engage with and be fastened to the nut, wherein releasing the handle bolt allows the rotation seat to pitch-rotate up and down in an angular range of 180 degrees, and the rotation seat is provided with a front-rear through hole and an open slot located above the front-rear through hole; and a light arm structure, which comprises a lighting device attached to an end of an arm rod and a circular rod having a grip, wherein the circular rod is first fit with a circular ring and a free end of the circular rod extends through the front-rear through hole to allow the free end of the circular rod to be coupled to rear end of the arm rod, so that the front-rear through hole receives the circular rod of the light arm structure to extend therethrough, an L-shaped bolt being fastened to the open slot in order to selectively fix a lighting direction of the lighting device so that releasing the bolt allows for adjustment of the lighting direction the lighting device in an angular range of a full circle of 360 degrees, the light arm structure being rotatably mounted to the pitch-rotation structure, the pitch-rotation structure being mounted to a top end of the extendible post structure, a lower end of the extendible post structure being mounted to the upright columnar frame of the base structure to form the omnidirectional lighting stand.

2. The omnidirectional lighting stand as claimed in claim 1, wherein the T-shaped member comprises a cross rod, casters being respectively mounted to two ends of the cross rod and a free end of each of the two elongate rods.

3. The omnidirectional lighting stand as claimed in claim 1, wherein the lighting device comprises a light-emitting diode (LED) based lighting device.

4. The omnidirectional lighting stand as claimed in claim 1, wherein the battery support tray receives a battery positioned thereon such that the battery is electrically connectable to the lighting device for supplying electrical power thereto.

* * * * *